Figure 1:
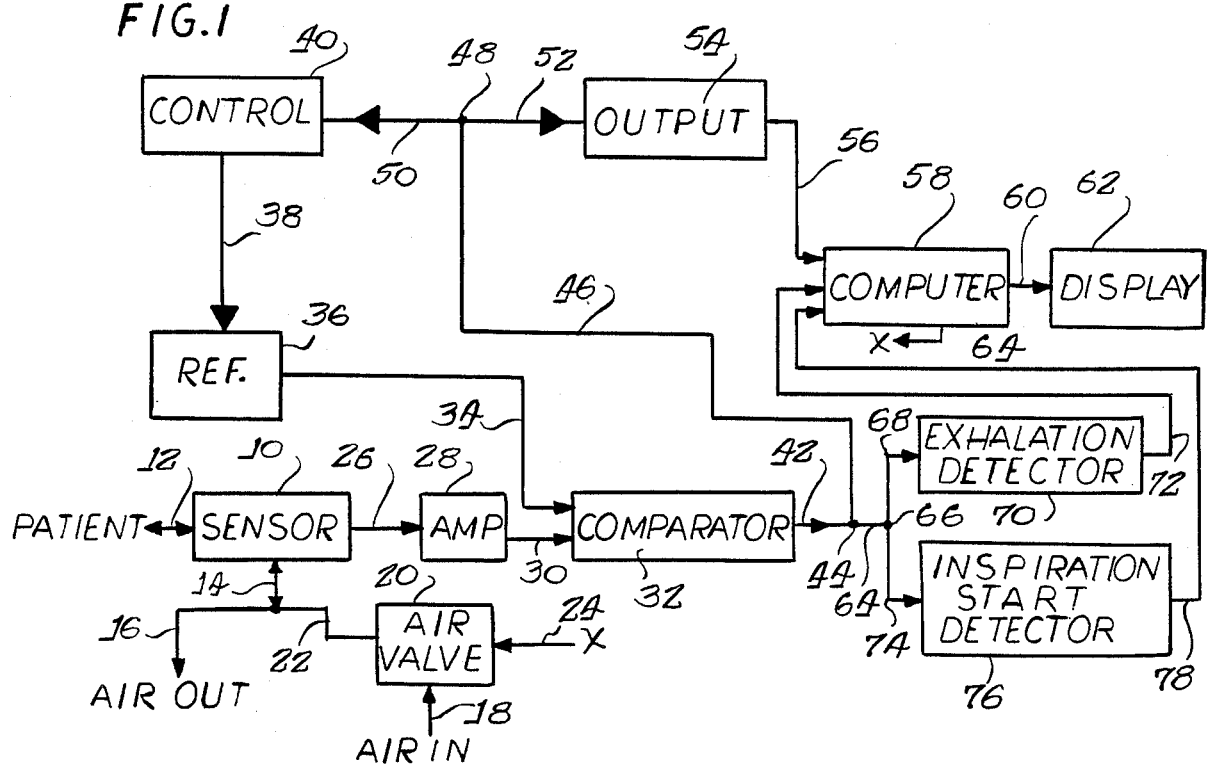

United States Patent [19]

Urman et al.

[11] Patent Number: 4,883,050
[45] Date of Patent: Nov. 28, 1989

[54] CIRCUIT PROVIDING INDICATION OF AIR ENTRAPMENT IN PATIENT'S LUNGS

[75] Inventors: Robert Urman, Schaumberg; Alfred G. Brisson, Kildeer; Cristopher Nowacki, Long Grove, all of Ill.

[73] Assignee: Nortgate Research, Inc., Arlington Heights, Ill.

[21] Appl. No.: 161,754

[22] Filed: Feb. 29, 1988

[51] Int. Cl.$^4$ ............................................. A62B 9/04
[52] U.S. Cl. ............................ 128/202.27; 128/201.23; 128/205.23
[58] Field of Search ........................ 128/719, 725–729, 128/205.23, 201.21, 201.23, 202.22

[56] References Cited
U.S. PATENT DOCUMENTS

| 3,867,934 | 2/1975 | Ollivier | 128/202.22 |
| 3,877,467 | 4/1975 | Plicchi | 128/202.22 |
| 3,911,899 | 10/1975 | Hattes | 128/205.23 |
| 4,187,842 | 2/1980 | Schreiber | 128/202.22 |
| 4,206,754 | 6/1980 | Cox et al. | 128/204.26 |
| 4,318,399 | 3/1982 | Berndtsson | 128/202.22 |
| 4,766,894 | 8/1988 | Legrand et al. | 128/204.21 |

Primary Examiner—Max Hindenburg
Assistant Examiner—K. M. Reichle
Attorney, Agent, or Firm—Robert M. Wolters

[57] ABSTRACT

A rate volume monitor includes a sensor which provides an output upon inspiration and upon expiration. If inspiration follows expiration too closely a computer operates an alarm to provide warning that air entrapment or "stacking" may occur in the patient's lungs.

3 Claims, 1 Drawing Sheet

CIRCUIT PROVIDING INDICATION OF AIR ENTRAPMENT IN PATIENT'S LUNGS

RELATED APPLICATIONS

The present application is related to copending applications of the same named inventors Ser. No. 07/077,746 filed July 27, 1987 for "Variable Threshold For Rate Volume Monitor" and Ser. No. 07/077,747 filed July 27, 1987 for "Timed Drift Compensation For Rate Volume Monitor". Those two applications and the present application are all assigned to the same assignee, Trutek Research, Inc. of Lake Zurich, Ill., an Illinois corporation.

BACKGROUND OF THE INVENTION

Some patients requiring respiratory assistance may be placed on what is known as a ventilator. The ventilator is typically connected through an endotracheal tube to the patient. A mixture of oxygen and air is periodically applied under pressure to force inhalation or inspiration by the patient. Exhalation is generally voluntary.

It is not desired for the patient to rest for too long a period between exhalation and inhalation. The forced inhalation is provided by a timer, which may be a part of a computer, so that inhalation is forced on a regular timed basis at a relatively short assumed time after the end of exhalation. Since the exhalation is generally voluntary, it is difficult to tell precisely when it will end, and thus when inhalation should start. It is known that expiration typically occurs approximately on a 2 to 1 time basis relative to inhalation. However, if the patient takes longer than assumed to complete exhalation, it is possible that a forced inspiration could start before exhalation was complete. This results in air entrapment or "stacking", and over a period of time enough air could be entrapped or stacked in a patient's lungs to cause blowing up or exploding of the patient's lungs with a severe danger of patient death.

OBJECTS AND BRIEF SUMMARY OF THE PRESENT INVENTION

The broad object of the present invention is to prevent air entrapment or "stacking" in a patient's lungs with forced ventilation.

More particularly, it is an object of the present invention to provide means of forwarding a warning to a monitoring nurse or technician if inspiration starts too soon after exhalation is completed, or before exhalation is completed.

In accordance with the teachings of the present invention, inspiration or inhalation is forced as timed by a computer. Inhalation and exhalation are monitored by a sensor which converts air flow to electrical potential, and allows the computer connected therewith to provide an indication of the volume of each breath, and accumulative volume of inhalation over a predetermined period of time. An exhalation detector and an inspiration start detector are triggered by the electrical signal developed by the sensor, and signals therefrom are connected to the computer so that the computer causes an alarm if the start of inspiration is too close in time to the end of exhalation.

THE DRAWINGS

Figure 2:
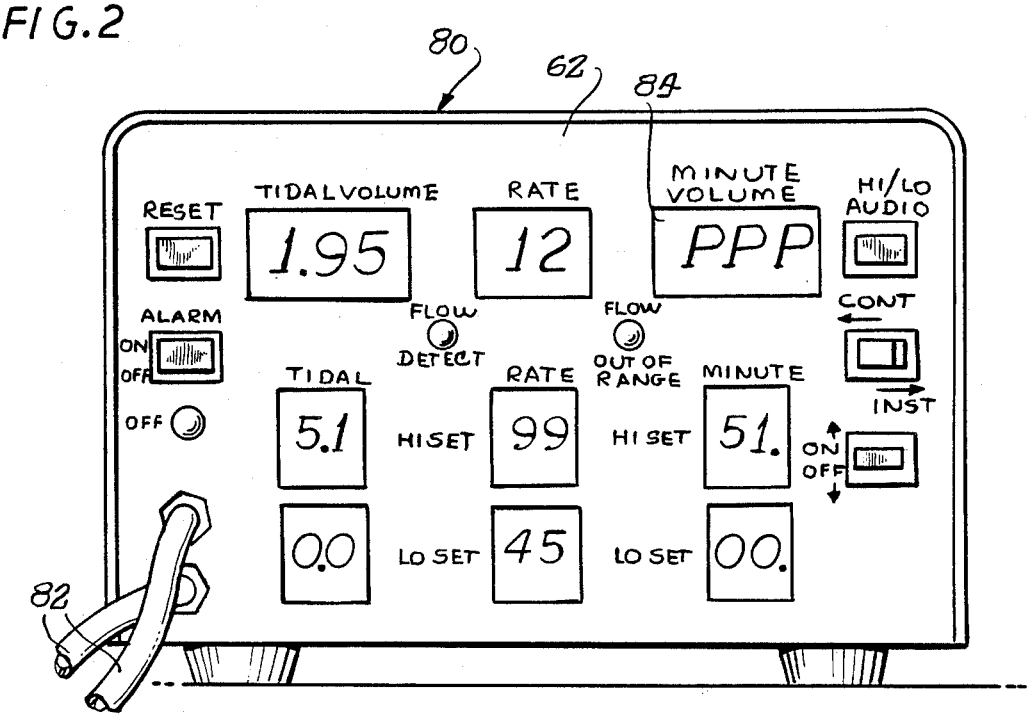

The present invention will best be understood with reference from the following specification when taken in connection with the accompanying drawings wherein:

FIG. 1 is a schematic electrical diagram illustrating the principles of the present invention; and FIG. 2 is a view of the front of a display monitor comprising a part of the present invention.

DETAILED DISCLOSURE OF THE ILLUSTRATED EMBODIMENT

Turning now in greater particularity to the drawings, and first to FIG. 1, there will be seen a sensor 10 which will be understood as including an air flow tube having a restriction therein, whereby pressure on opposite sides of the restriction is different. The sensor further includes an electrical transducer connected to air pressure sensing connections on the opposite sides of the restriction in the air flow tube. Air is indicated as going to and from the patient at 12 through the sensor, and air is indicated as passing into the sensor tube and out of the sensor at 14. Air out continues at 16 and simply vents to atmosphere. Air in actually comprises in most instances a mixture of air and oxygen, and is supplied from a suitable source at 18 to a valve at 20, from which it leads at 22 to the air in and out flow tube 14. The air in valve 20 is controlled by an electrical connection 24, and indicated at X; the remainder of the connection at X leading to electrical control input at 24 will be disclosed hereinafter.

The electrical output of the sensor at 26 is connected to a suitable electronic amplifier 28. The output of the amplifier at 28 is connected at 30 to the input of a comparator 32. A reference voltage is applied to the comparator at 34 from a voltage reference 36. It is known that the output sensor may drift somewhat with time, and accordingly means is connected to the reference source 36 at 38 from a control circuit 40. The output of the comparator 32 at 42 is connected to a junction 44, and from this point there is a feedback line 46 which leads to a junction 48, and from the junction 48 through input 50 to the control circuit 40. The resetting of the reference level 36 under control of the control circuit 40 is detailed in our copending application Ser. No. 07/077,746, referenced above.

Connection is made from the junction 48 through a conductor 52 to an output circuit 54 which leads through an input connection 56 to a computer 58. The computer has an output at 60 connected to a display 62. The computer further has an output at 64 leading to the connection X and providing the electrical input at 24 to the air in valve 20.

The junction 44 is connected by a conductor 64 to a further junction 66. This junction leads through an input connection 68 to an exhalation detector 70, which provides an output signal when exhalation drops below a certain threshold on a conductor 72 leading to an input of the computer 58. The junction 66 also leads through a conductor 74 to an inspiration start detector 76, the output of which is connected by a conductor 78 to an input of the computer 58.

All of the foregoing parts save for the air flow connections including the pneumatic portion of the sensor 10 can be included in a rate volume monitor 80 shown in FIG. 2, and providing the display 62. The pneumatic portion of the sensor is connected by a pair of pressure conveying tubes 82 to the front of the rate volume monitor 80 and to the air pressure to electric voltage converting device. Most of the information revealed by the display at 62 is not directly relevant to the present invention, and will be well understood by those familiar with rate volume monitors. The important thing is that the minute volume display 84 normally reads in numerals, indicating minute volume in three figures to one decimal place. The computer 58, among its other functions serves as a timing means for the inhalation and exhalation detectors, and if it twice in succession measures the start of inspiration less than 0.15 second after the exhalation detector has provided a signal that exhalation has dropped below the predetermined threshold, the minute volume changes to indicate PPP, as is shown at 84 in FIG. 2. The PPP display is not a static display, but alternates with the numerals indicating current minute volume, thereby providing a flashing display which will catch the eye of the nurse or other attendant. The nurse or other attendant thus is alerted to the potential for air entrapment in a totally mechanically ventilated patient. The indication may or may not be appropriate for a patient who is breathing spontaneously, due to the wide variation of spontaneous breathing patterns observed. In particular, it is quite possible for a spontaneously breathing patient to go immediately from exhalation to inspiration, especially if breathing at a high rate, thus not allowing 0.15 second interval to occur. However, the operator is alerted to the possibility of air entrapment or "stacking". Another determination of time from the end of exhalation to the start of insparation is made for each breath. Each time a check is made to see if there are two successive indications of time less than the predetermined 0.15 second. If there are not two such short periods in succession, then, then the PPP is cancelled, and the minute volume is indicated alone.

The specific example of the invention as herein shown and described is for illustrative purposes only. Various changes in structure will no doubt occur to those skilled in the art, and will be understood as forming a part of the present invention insofar as they fall within the spirit and scope of the appended claims.

The invention is claimed as follows:

1. Apparatus for patient ventilation comprising forced ventilation means for connection to a patient, sensor means connected to said ventilation means for producing an electrical signal in accordance with air flow on inspiration and on expiration, first signal means connected to said sensor means for detecting when expiration drops below a predetermined threshold and producing a first electrical output in accordance therewith, second signal means connected to said sensor means and producing a second electrical output upon start of inspiration, timing means to which said first and second signal means are connected and producing a third electrical output if said first and second electrical outputs are closer in time than a predetermined time, and alarm means to which said third electrical output is connected and providing an alarm if a plurality of said first and second electrical outputs are closer in time than said predetermined time.

2. Apparatus as set forth in claim 1 wherein said alarm means produces an additional signal, and wherein said alarm and said additional signal alternate.

3. Apparatus as set forth in claim 2 wherein said alarm means comprises a visual alarm means.

* * * * *